United States Patent [19]

Hazen

[11] Patent Number: 5,324,198

[45] Date of Patent: Jun. 28, 1994

[54] DENTURE COVERING EXISTING TEETH AND GUMS

[76] Inventor: Anthony P. Hazen, 4010 E. 53rd St., Tulsa, Okla. 74135-4816

[21] Appl. No.: 897,762

[22] Filed: Jun. 12, 1992

[51] Int. Cl.⁵ .................... A61C 13/00; A61C 13/08
[52] U.S. Cl. ..................................... 433/171; 433/167
[58] Field of Search ................ 433/167, 172, 215, 171

[56] References Cited

U.S. PATENT DOCUMENTS

| 277,933 | 5/1883 | Richmond | 433/172 |
| 973,343 | 10/1910 | Corcoran | 433/172 |
| 3,716,918 | 9/1971 | Tole et al. | 433/172 |
| 4,580,980 | 4/1986 | Acquanetta | 433/167 |
| 4,764,115 | 8/1988 | Willits et al. | 433/177 |
| 5,018,533 | 5/1991 | Hawkins | 128/848 |

*Primary Examiner*—Gene Mancene
*Assistant Examiner*—Cindy A. Cherichetti

[57] ABSTRACT

This device includes two separate impression-molded all gum and cap-cup encasements (upper and lower arches) with veneered artificial teeth mounted to the encasement walls. The veneered encasements comprise the completed all gum and cap-cup dental device. The completed cap-cup encasements cover the upper and lower arches of full sets of natural teeth and gums.

2 Claims, 2 Drawing Sheets

DENTURE COVERING EXISTING TEETH AND GUMS

BACKGROUND OF THE INVENTION

The present invention relates to prosthetic denture devices. However, its application and relative functional use differs. Denture devices provide teeth where there are none, but should be in direct position and proportion to the underlying vacated gum.

This device goes over existing teeth and gums, and bridges over missing teeth where possible.

The present invention relates to prosthetic dental caps and/or crowns. However, the application and relative functional use of this invention differs. Caps and/or crowns are permanently affixed to the teeth. This device is not permanently affixed to the teeth.

In design appearance this device differs from caps and/or crowns in that it is one whole unit rather than multiple units, as used in caps and/or crowns.

SUMMARY OF INVENTION

It is the object of this invention to cover whole sets of human teeth, palate and gums [upper and/or lower arch devices] in an aesthetically pleasing skeletal-dental prosthetic device constructed from all types of approved prosthetic dental materials, i.e., acrylics, plastics, vinyl, hard and soft rubbers, metals, silicone, and gold, and/or combinations thereof.

It is the intension of this device, when properly used and prescribed, to produce superior, functional and oral hygiene which will result in extended life to the teeth.

It is also the intention of this device to supply the cosmetic dental industry with a new and unique method and dimension in asesthetically pleasing artificial teeth and gums. The reuslt is happy users with a new design in teeth never available to them before now.

DESCRIPTION OF THE PREFERRED EMBODIMENT

The dental device includes an all gum tooth cap-cup encasement 1 constructed from dental material which artificial veneer teeth 2 are joined or mounted to the wall of the encasement cup. The encasement cup is perforated with periodic circulation holes 3. The gum and teeth encasement is created from an impression-mould of the user's teeth and gums.

The device may be constructed from all approved prosthetic dental materials and combinations thereof, i.e., acrylics, plastics, silicone, vinyls, hard and soft rubbers, metals and gold. The variations of the construction design and use of these materials are determined by the dentist according to the user's needs.

Figure 1:
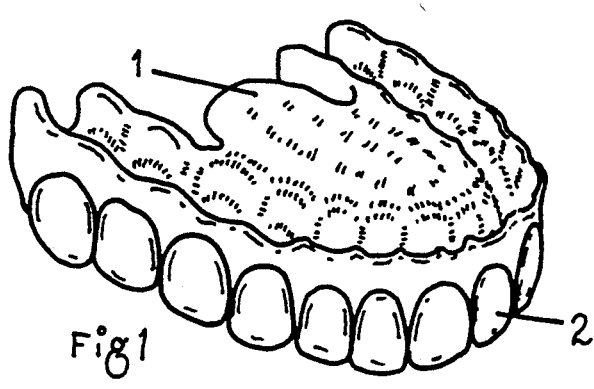
FIG. 1 is a perspective view of a dental device for the upper arch.
Figure 3:
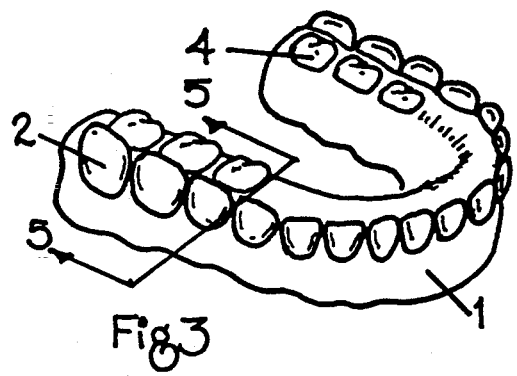
FIG. 3 is a perspective view of a dental device for the lower arch.
Figure 2:
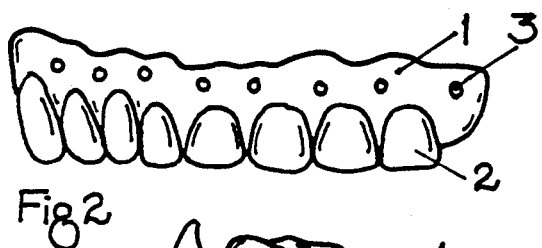
FIG. 2 is a side view of the dental device for the upper arch of FIG. 1.
Figure 4:
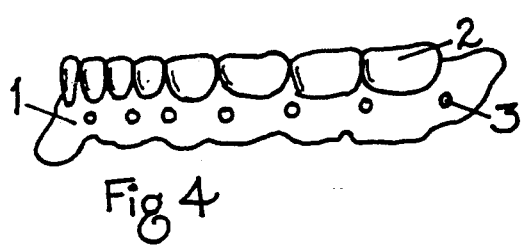
FIG. 4 is a side view of the dental device for the lower arch of FIG. 3.
Figure 5:
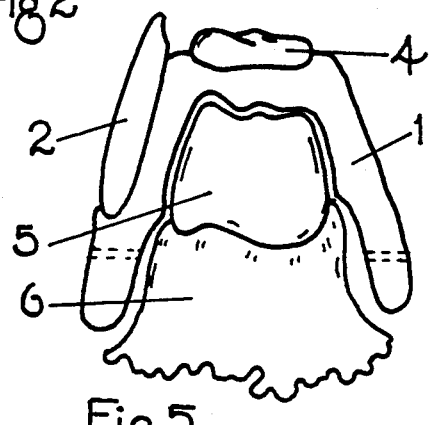
FIG. 5 is a Section view along the line 5—5 of FIG. 3.
Figure 6:
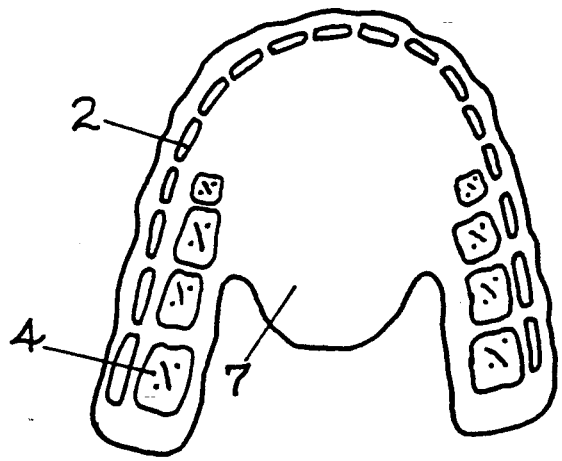
FIG. 6 is a bottom view of FIG. 1.
Figure 7:
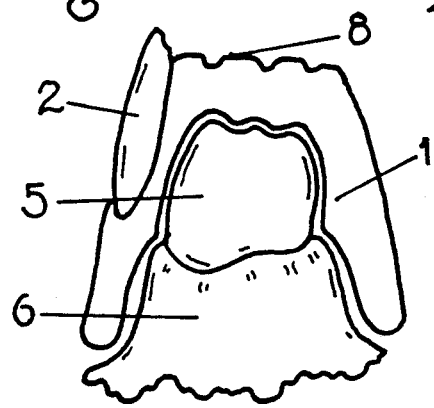
FIG. 7 is a section view of an alternative embodiment without bottom veneers.
Figure 8:
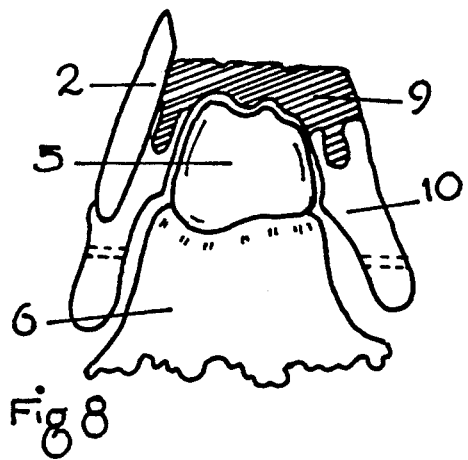
FIG. 8 is a section view of an alternative embodiment having a cast metal bottom and plastic encasement.
Figure 9:
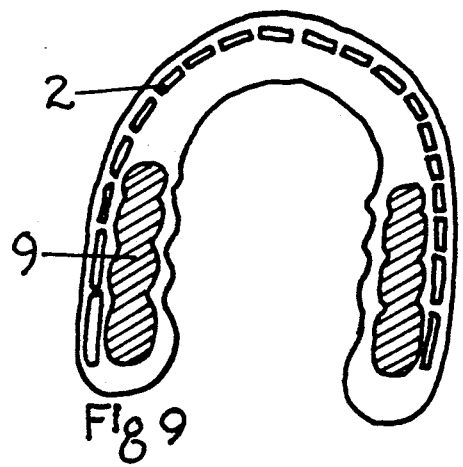
FIG. 9 is a bottom view of a lower arch of FIG. 8.
Figure 10:
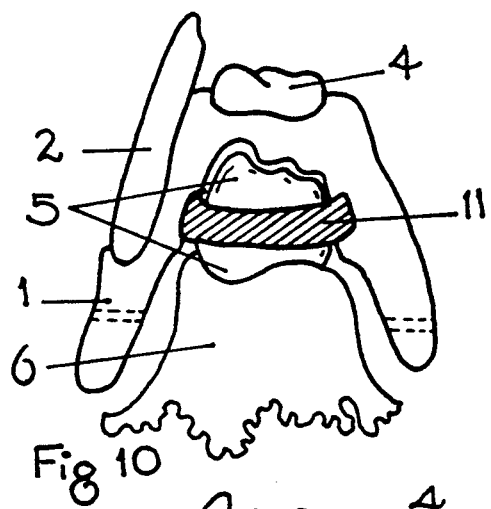
FIG. 10 is a section view of an alternative embodiment having brace bands.
Figure 11:
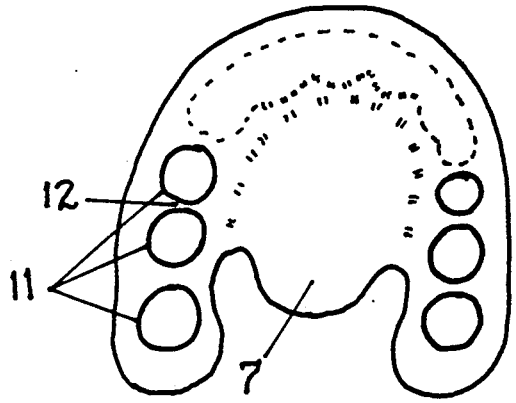
FIG. 11 is a bottom view of the upper arch of FIG. 10.
Figure 12:
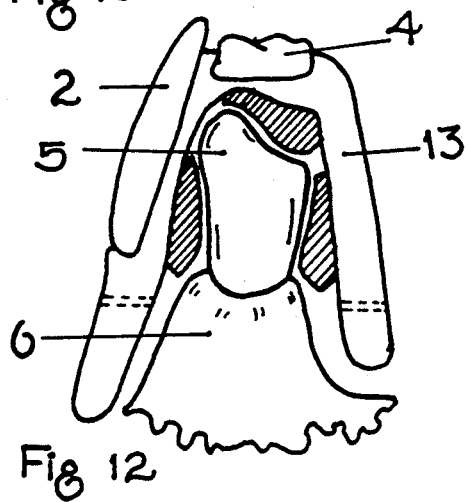
FIG. 12 is a section view of an alternative embodiment with a co-soft liner.
Figure 13:
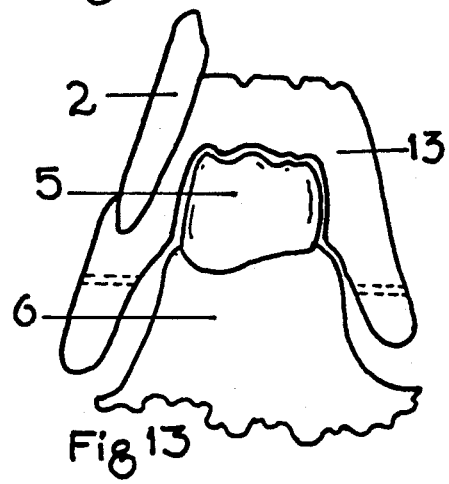
FIG. 13 is a section view of an alternative embodiment with a metal encasement.

Some other possible construction design and material variations are represented in FIGS. 2 thru 7.

List of the elements
1. encasement
2. side veneers
3. circulation holes
4. bottom veneers
5. tooth
6. gum
7. palate
8. molded plastic surface without bottom veneer
9. cast metal bottom
10. plastic encasement
11. brace band
12. plastic fill
13. all metal encasement

I claim:

1. A removable prosthetic dental device for enhancing the facial appearance by providing aesthetically pleasing artificial teeth for non-denture wearers, for bridging spaces left by missing teeth, for protecting damaged or hypersensitive teeth form temperature extremes, and for strengthening the user's ability to more effectively masticate food comprising;

an encasement constructed from approved dental materials and taken from an impression mold of the user's natural teeth and gums, said encasement having inner encasement walls partially lined with co-soft material for abutting the user's natural teeth and gums and outer encasement walls, and a plurality of artificial teeth ground down to veneers and mounted on said outer encasement walls.

2. The removable prosthetic dental device of claim 1 further comprising;

bottom veneers mounted on a bottom of the outer encasement walls.

* * * * *